United States Patent [19]

Doty et al.

[11] Patent Number: 5,562,919
[45] Date of Patent: Oct. 8, 1996

[54] DRIED ANIMAL PLASMA AS A PHARMACEUTICAL EXCIPIENT FOR COMPRESSED TABLET FORMULATION

[75] Inventors: Brian D. Doty, Phoenixville, Pa.; Mark Meyer, Ames, Iowa

[73] Assignee: American Meat Protein Corporation, Ames, Iowa

[21] Appl. No.: 64,951

[22] Filed: May 20, 1993

[51] Int. Cl.⁶ ....................................... A61K 9/20
[52] U.S. Cl. .................. 424/464; 424/468; 424/530; 514/960; 514/961
[58] Field of Search .................... 424/464, 468, 424/530; 514/960, 961

[56] References Cited

U.S. PATENT DOCUMENTS

| | | | |
|---|---|---|---|
| 4,767,789 | 8/1988 | Blank et al. | 424/464 |
| 4,792,452 | 12/1988 | Howard et al. | 424/468 |
| 5,279,832 | 1/1994 | Greissinger et al. | 424/464 |

OTHER PUBLICATIONS

Doty, Brian D. "An Evaluation of AP–720 in Pharmaceutical Dosage Forms.", Dissertation Jan. 1988.

*Primary Examiner*—James J. Seidleck
*Assistant Examiner*—John M. Cooney, Jr.
*Attorney, Agent, or Firm*—Zarley, McKee, Thomte, Voorhees & Sease

[57] ABSTRACT

This invention relates to the use of purified spray dried animal plasma as a binder for tablet pharmaceutical compositions. Spray dried plasma demonstrates good tablet formation as a direct compression vehicle or solution binder, for conventional and sustained release compositions.

33 Claims, 5 Drawing Sheets

FIG.3
□ HPMC
◇ PVP-40
▨ AVICEL PH101
◆ AP-720

FIG.4
○ FORMULATION 12 (45 MG THEO)
△ FORMULATION 13 (60 MG THEO)
□ FORMULATION 11 (30 MG THEO)

FIG.5
□ FORMULATION 24 (25 MG THEO)
△ FORMULATION 25 (50 MG THEO)
○ FORMULATION 26 (100 MG THEO)

FIG.6A
▨ FORMULATION 14 IN .05% KCl
◇ FORMULATION 14 IN 0.1% KCl
□ FORMULATION 14 IN 0.5% KCl

FIG.6B

□ FORMULATION 32 IN .01N HCL
◇ FORMULATION 25 IN .01N HCL
▨ FORMULATION 25 IN D.W.
◇ FORMULATION 32 IN D.W.

FIG.7

□ FORMULATION 32 IN GI
◆ FORMULATION 25 IN GI
▨ FORMULATION 25 IN DW
◇ FORMULATION 32 IN DW

FIG. 8

□ FORMULATION 56(HPMC/THEO)
◇ FORMULATION 26(AP-720/THEO)

DRIED ANIMAL PLASMA AS A PHARMACEUTICAL EXCIPIENT FOR COMPRESSED TABLET FORMULATION

BACKGROUND OF THE INVENTION

It is estimated that over 90% of all drugs used to produce a systemic effect are administered by the oral route. Of all drugs that are administered orally, solid oral dosage forms represent the preferred class of product. These oral tablet dosage forms include several benefits: they are a unit dose form, offering the least content variability, they are inexpensive, they are the lightest and most compact of all oral dosage forms, they are the easiest and cheapest to package and ship, product identification is simple and cheap, they have greatest ease of swallowing especially when coated, they easily lend themselves to certain special-release profile products such as enteric or delayed-release products, they are better suited to large-scale production, and have the best combined properties of chemical, mechanical and microbiologic stability of all oral forms. Another important consideration is that the tablets are relatively tamper resistant.

The tableting process generally includes compressing various formulations into a compact unit by means of a tablet press. A tablet press using a punch and die set is traditionally used and can produce large amounts of tablets in a short period of time.

Compressed tablet formulations currently are produced by using one of three general methods: wet granulation; double compaction (dry granulation); or direct compression. Direct compression involves only the mixing and compression of a formulation. Despite its ease and lesser cost due to less processing time and energy involved, direct compression is rarely used because very few substances exhibit good flow and compaction.

Wet granulation is currently the most widely used method. This process binds powders together with an adhesive instead of compaction. The technique involves incorporation of binder solution, slurry or suspension into the powder mixture while mixing or the binder may be incorporated into the powder mixture and subsequently wetted while mixing and then compressed.

The dry granulation method involves the initial compaction of a formulation into slugs by means of flat-faced punches or roller compactors. The slugs are then screened or milled into granules for tableting.

Very few active medicaments will flow freely, directly compress, or are dosed at strengths that make the tablet easily handled for oral administration. It is often necessary to incorporate other products into a formulation to improve stability, aid in manufacture and aid in performance of the dosage form. These ingredients (excipients) must be non-toxic, must not be contraindicated themselves (such as sucrose or sodium) and must be physiologically inert, physically and chemically stable by themselves and in combination with drugs, and finally they must have no deleterious effect on bioavailability of the drugs. Tablet preparation additives include bulking agents, binding agents, lubricants, gildants, disintegrants, coloring agents and flavoring agents.

Probably one of the most important excipients are binding agents that impart particle cohesiveness to the tablet formulation which insures that the tablet will remain intact after compression. Further, granulating with binders may improve the free flowing qualities of a formulation which is needed to pass through a high speed tablet press. Materials commonly used as binders include starch, gelatin, and sugars such as sucrose, glucose, dextrose, molasses, and lactose. Natural and synthetic gums also have been used including acacia, sodium alginate, carboxymethylcellulose, methylcellulose and polyvinylpyrrolidone. Other agents which may be considered binders under certain circumstances include polyethylene glycol, ethylcellulose and some waxes. Binders may be used in solution or in the dry form depending on the other ingredients in the formulation and method of preparation. The proper binder/solvent system must be selected to obtain the desired properties for a tablet.

As can be seen, a continuing need exists in the art for new excipients which may be used in solid oral dose form pharmaceutical preparations. This invention relates to the use of spray dried animal plasma as an excipient for tablet pharmaceutical formulations. Spray dried animal plasma exhibits the properties of a good binder as well as properties for a direct compression vehicle and a sustained release vehicle, the latter two uses include novel uses for protein substances.

It is an object of the present invention to provide a protein excipient which is cost effective and which may be used in pharmaceutical compositions.

A further object of the present invention is directed to the use of spray dried animal plasma as a tablet binder.

Another object of the present invention is to provide a method of preparation of pharmaceutical tablets.

Yet another object of the present invention is to provide a protein excipient which may be used as a direct compression vehicle and a sustained release vehicle.

A further object of the present invention is to provide a tablet binder which maintains tablet integrity, is chemically inert, and will sustain prolonged drug release.

Further objects of the invention will become obvious from the detailed description of the invention which follows.

SUMMARY OF THE INVENTION

This invention relates to the use of dried animal plasma as an excipient for pharmaceutical tablet compositions. Animal plasma is separated from animal blood, concentrated, and is dried to form a powder material. The dried plasma is then combined with a medicament and formed into tablets by standard techniques.

DETAILED DESCRIPTION OF THE INVENTION

According to the present invention, plasma obtained from animal sources is dried to form a powder-like substance which is used to form pharmaceutical tablet oral delivery medicaments. The purified plasma is obtained by collecting blood from animals, preferably pigs or cows. For example, blood may be collected at slaughter plants, provided it is separated according to species. As it is collected, the blood should be held in a circulating tank with anticoagulants such as sodium citrate or sodium phosphate to avoid clotting. The whole blood is then separated, likely by centrifugation into two parts, cellular material (red corpuscles, white corpuscles and platelets) and plasma. Plasma proteins are composed of about 60% albumin and about 40% globulin. After separation the plasma is cooled 45° F. to retard growth of bacteria and stored in an insulated tanker if necessary.

The plasma component is then further concentrated 2 to 3 fold by membrane filtration and finally is dried to form a beige powdery substance. Drying may occur by spray drying, oven drying, vacuum drying, freeze drying. Spray drying should occur at temperatures low enough to maintain the highly digestible proteins but high enough to purify the dry powder eliminating bacterial and viral contamination. Traditionally an inlet temperature of approximately 400° F. is used and an outlet temperature of 180°–200° F. The resulting powdery substance may then be combined with the desired medicament or active substance and tabletized by traditional pharmaceutical procedures.

Spray dried plasma has traditionally been used as a high quality protein used as a replacement for milk proteins due to its high immunoglobulin content. This plasma has also been used in the feed industry as a feed additive for swine, veal aquaculture and pet food for its influence on voluntary feed intake and efficient gains equal to or better than milk proteins. The protein powder contemplated by this invention is comprised primarily of amino acids. A typical amino acid assay of the powder by acid hydrolysis and subsequent column chromatography results in the following amino acid concentrations in grams per 100 grams of protein:

|  | From Beef Sources | From Pork Sources |
| --- | --- | --- |
| Alanine | 8.00 | 4.36 |
| Aspartic Acid | 10.07 | 9.21 |
| Arginine | 5.18 | 6.23 |
| Cystine | 1.08 | 3.24 |
| Phenylalanine | 5.10 | 5.36 |
| Glycine | 5.20 | 3.53 |
| Glutamic Acid | 11.91 | 12.81 |
| Histidine | 4.63 | 3.62 |
| Isoleucine | 2.90 | 2.84 |
| Leucine | 9.88 | 8.05 |
| Lysine | 8.93 | 8.83 |
| Methionine | 1.40 | 0.77 |
| Proline | 5.44 | 5.92 |
| Serine | 5.25 | 5.59 |
| Threonine | 5.90 | 5.98 |
| Tryptophan | .74 | 1.93 |
| Tryosine | 3.45 | 5.07 |
| Valine | 7.32 | 5.96 |

Chemical and other properties of the powder protein include 70–75% protein, 7% moisture, 2% fat, 7% carbohydrates, pH 9, aqueous solubility 90% minimum; salmonella negative, standard plate count less than 20,000 per gram; and molecular weight range 40,000 to 820,000 daltons.

It is important to note that moisture levels must be kept at a minimum during spray drying and the powder should be stored in moisture resistant containers.

The powder may then be combined with an active medicament and other additives known in the field of the invention to form a tablet. There are several types of tablets useful for this invention. These include compressed or standard compressed tablets, multiple compressed tablets, repeat-action tablets, delayed-action and enteric coated tablets, sugar- and chocolate-coated tablets, film-coated tablets and chewable tablets. Compressed tablets or standard compressed tablets are produced by compression of a formulation into a compact means by machinery.

The weight ratio of active medicament to excipient can vary widely depending upon the nature of the active medicament, the unit dose and the nature of the tableting process.

For compressed tablet dose forms the weight ratio of active medicament to plasma excipient should generally be within the range of 0.01 to 1 to 1:2 with a preferred range of 0.1 to 1 to 1:1.

The term "medicament" is used herein to refer to a broad class of useful chemical and therapeutic agents including physiologically active steroids, antibiotics, antifungal agents, antibacterial agents, antineoplastic agents, analgesics and analgesic combinations, anorexics, anthelmintics, antiarthritics, antiasthma agents, anticonvulsants, antidepressants, antidiabetic agents, antidiarrheals, antihistamines, anti-inflammatory agents, antimigraine preparations, antimotion sickness preparations, antinauseants, antiparkinsonism drugs, antipruritics, antipsychotics, antipyretics, antispasmodics, including gastrointestinal and urinary; anticholinergics, sympathomimetics, xanthine derivatives, cardiovascular preparations including calcium channel blockers, betablockers, antiarrhythmics, antihypertensives, diuretics, vasodilators including general coronary, peripheral and cerebral; central nervous system stimulants, cough and cold preparations, decongestants, hormones, hypnotics, immunosuppressives, muscle relaxants, parasympatholytics, parasympathomimetics, psychostimulants, sedatives, tranquilizers, allergens, antihistaminic agents, anti-inflammatory agents, physiologically active peptides and proteins, and the like.

Tests run on tablet formulations using spray dried animal plasma demonstrated its overall utility in virtually all tablet formulations. Granulations for traditional release tablets and sustained release showed a good flow rate and angle of repose. The binder was shown to have an acceptable level of moisture uptake.

Further, tablets using spray dried animal plasma demonstrated good binding and tablet strength in both direct compression and solution binding formulations.

Importantly, spray dried animal plasma was shown to be an excellent sustained release excipient in both direct compression systems and in combination with a water insoluble filler. Delayed action or sustained release dosage forms optimize therapeutic efficiency, patient compliance and safety and are an important use for this plasma. Sustained action dosage forms may be developed by decreasing the rate of dissolution and thereby drug absorption. Potential advantages of sustained drug therapy include increased patient compliance, less total drug to minimize or eliminate side effects, maintaining drug blood levels consistently in the therapeutic range and lower cost of therapy due to less doses. Controlled release tablet formulations may be developed using spray dried animal plasma as a binder at high concentrations. The spray dried animal plasma forms a hydrogel when exposed to an aqueous medium. Thus sustained release of the drug may be obtained by the formation of the barrier in which the drug must diffuse through or release by relaxation of the polymer. In fact as a direct compression vehicle sustain release formulation, spray dried animal plasma was found to perform better than hydroxypropyl methyl cellulose. All sustained release formulations were found to be released up to 12 hours and release rate was unaffected by drug load, drug solubility, and dissolution media including ionic strength, pH, and simulated gastrointestinal environment.

EXAMPLES

Blood from pigs was collected from various slaughter plants around Iowa including Storm Lake, Iowa; St. Joseph, Mo., and Perry, Iowa. The blood was held in a tank with 5 grams per liter sodium citrate added to prevent clotting. The blood was then separated in a continous centrifuge (Alphalaval Model 392). The supernatant plasma was collected, and cooled in a Chester Jensen plate chiller to 45° F. The plasma was further concentrated twofold by membrane filtration using a reverse osmosis system and finally spray dried, with a Blau Knox Model 750 Spray Dryer. The powder, under the trade name of AP-720, was then used in a number of formulations and tableting procedures to examine physical, chemical and bioavailability properties of the resulting tablet.

FORMULATIONS INVOLVING AP-720

A) Conventional Release Tablets - Granulation, Compression

Several experimental formulations were made using AP-720 as the binder to evaluate tablet formulas when tested by established methods. A list of the different formulations is disclosed in Table 1. Solution binding formulations are disclosed in Table 5.

TABLE 1

Tablet formulations

| No | AP-720 | Dicalcium phosphate | Lactose NF | AcDiSol ® | CPM | Anhydrous theophylline | PPA | APAP | Mag. Stearate | Process |
|---|---|---|---|---|---|---|---|---|---|---|
| 1 | 45 mg | 222 mg | — | — | — | — | — | 30 mg | 3 mg | g,c |
| 2 | 287 mg | — | — | — | — | 10 mg | — | — | 3 mg | g,c |
| 3 | 147 mg | — | — | — | — | 150 mg | — | — | 3 mg | g,c |
| 4 | 287 mg | — | — | — | 10 mg | — | — | — | 3 mg | dc,x |
| 5 | 45 mg | 222 mg | — | — | 30 mg | — | — | — | 3 mg | g,c |
| 9 | 6 mg | — | 186 mg | 4 mg | 4 mg | — | — | — | 2 mg | g,c |
| 10 | 45 mg | 144 mg | — | — | 8 mg | — | — | — | 3 mg | g,c |
| 11 | 45 mg | 222 mg | — | — | — | 30 mg | — | — | 3 mg | g,c |
| 12 | 45 mg | 207 mg | — | — | — | 45 mg | — | — | 3 mg | g,c |
| 13 | 45 mg | 192 mg | — | — | — | 60 mg | — | — | 3 mg | g,c |
| 14 | 45 mg | 244 mg | — | — | 8 mg | — | — | — | 3 mg | g,c |
| 15 | 287 mg | — | — | — | 10 mg | — | — | — | 3 mg | dc |
| 16 | 277 mg | — | — | — | 20 mg | — | — | — | 3 mg | dc |
| 17 | 267 mg | — | — | — | 30 mg | — | — | 10 mg | 3 mg | dc |
| 18 | 287 mg | — | — | — | — | — | — | 10 mg | 3 mg | dc |
| 19 | 247 mg | — | — | — | — | — | — | 50 mg | 3 mg | dc |
| 20 | 197 mg | — | — | — | — | — | — | 100 mg | 3 mg | dc |
| 21 | 287 mg | — | — | — | — | — | 10 mg | — | 3 mg | dc |
| 22 | 287 mg | — | — | — | — | 10 mg | — | — | 3 mg | dc |
| 23 | 189.8 mg††† | — | — | — | 10 mg | — | — | — | 0.2 mg | dc |
| 24 | 174.8 mg | — | — | — | — | 25 mg | — | — | 0.2 mg | dc |
| 25 | 149.8 mg | — | — | — | — | 50 mg | — | — | 0.2 mg | dc |
| 26 | 99.8 mg | — | — | — | — | 100 mg | — | — | 0.2 mg | dc |
| 27 | 189.8 mg††† | — | — | — | 10 mg | — | — | — | 0.2 mg | dc |
| 28 | 189.8 mg††† | — | — | — | 10 mg | — | — | — | 0.2 mg | dc |
| 29 | 149.8 mg††† | — | — | — | — | 50 mg | — | — | 0.2 mg | dc |
| 30 | 99.8 mg††† | — | — | — | — | 100 mg | — | — | 0.2 mg | dc |
| 31 | 188 mg† | — | — | — | 10 mg | — | — | — | 2 mg | dc |
| a | 188 mg 20/25 | — | — | — | 10 mg | — | — | — | 2 mg | dc |
| b | 188 mg 25/30 | — | — | — | 10 mg | — | — | — | 2 mg | dc |
| c | 188 mg 30/40 | — | — | — | 10 mg | — | — | — | 2 mg | dc |
| d | 188 mg 40/60 | — | — | — | 10 mg | — | — | — | 2 mg | dc |
| e | 188 mg††† | — | — | — | 10 mg | — | — | — | 2 mg | dc |
| 32 | 189.8 mg††† | — | — | — | 10 mg | — | — | — | 0.2 mg | dc |
| 33 | 189.8 mg††† | — | — | — | 10 mg | — | — | — | 0.2 mg | dc | g = granulation,
c = compression,
dc = direct compression,
x = Opadry ® coated tablets.
t = distribution,
††† = 60/80 mesh fractions.

Conventional release tablets were prepared by using granulation and compression in accordance with the following description, which details the procedure for formulation number 9.

Chlorpheniramine maleate (Sigma Chem. Co.) was used as a model drug substance to determine the release patterns from the dosage form. Chlorpheniramine maleate was dosed at low strengths and should not affect the overall properties of the formulation. The components of formulation 9 are posted below.

| Substance | Concentration | Use |
|---|---|---|
| Lactose NF | | Bulking agent |
| Chlorpheniramine maleate | 4 mg/tablet | Active |
| AP-720 | 3% (w/w) | Binder |
| Magnesium Stearate | 1% (w/w) | Lubricant/Glidant |
| AcDiSol ® | 1% internal/ 1% external | Disintegrant |
| Distilled water (40 ml) | | Wetting agent |

Tablet weight = 100 mg
Batch size = 200 grams
Theoretical Yield = 2000 tablets

1) Preparation and Testing of Granules

Granulation of the formulation was conducted by conventional massing and screening techniques. In formulation 9 the lactose NF (Ruger), drug, 1% AcDiSol ® (FMC Corp.) and AP-720 were initially mixed in a planetary mixer (Hobart) for 10 minutes. The wetting agent was slowly incorporated into the powder mixture over a period of 5 minutes while mixing at low speed. The resultant mass was dried overnight at 40° C. in a Stokes vented tray drying oven. The granules formed were then passed through #20 mesh screen with the aid of an Erweka oscillating granulator. The reduced granules were tested for flow rate, angle of repose as well as bulk and tap density and loss on drying. Magnesium stearate (Ruger) and 1% AcDiSol ® were then added and mixed in a twin shell blender (Patterson-Kelly Co. Inc. model LB-1384) for 10 minutes. The lubricated granular flow rate was then determined. Table 2 depicts flow rate and angle of repose data for several formulations.

TABLE 2

Flow rates and angles of repose for several AP-720 formulations

| Formulation | Process | Unlubricated Gran. Flow Rate (g/sec) | Lubricated Gran. Flow Rate (g/sec) | Angle of Repose |
|---|---|---|---|---|
| 4 | Direct Compression | — | 13.8 | — |
| 6 | Direct Compression | no flow | no flow | — |
| 7 | Direct Compression | 10.5 | 10.8 | 32 |
| 8 | Direct Compression | 10.5 | 10.8 | 32 |
| 9 | Granulation | 12.0 | 7.0 | 25.2 |
| 10 | Granulation | 18.73 | 19.4 | 25.4 |
| 11 | Granulation | 20.1 | 16.7 | 27.3 |
| 12 | Granulation | 21.6 | 15.6 | 30.4 |
| 13 | Granulation | 19.9 | 14.3 | 29.1 |
| 14 | Granulation | 18.7 | 19.4 | 25.4 |
| 19 | Direct Compression | 7.3 | 9.38 | — |
| 20 | Direct Compression | no flow | no flow | — |
| 23 | Direct Compression | — | 13.8 | — |
| 24 | Direct Compression | — | 12.2 | — |
| 25 | Direct Compression | — | 10.8 | — |
| 26 | Direct Compression | — | 9.7 | — |
| 27 | Direct Compression | — | 13.8 | — |
| 28 | Direct Compression | — | 13.8 | — |
| 29 | Direct Compression | — | 10.8 | — |
| 30 | Direct Compression | — | 10.8 | — |
| 31 Distribution | Direct Compression | 10.7 | 7.8 | 24.8 |
| 20/25 mesh | Direct Compression | 10.3 | 10.0 | 24.4 |
| 25/30 mesh | Direct Compression | 10.1 | 10.0 | 26.5 |
| 30/40 mesh | Direct Compression | 10.6 | 10.0 | 23.9 |
| 40/60 mesh | Direct Compression | 11.2 | 5.7 | 23.9 |
| 60/80 mesh | Direct Compression | 12.2 | 5.0 | 20.3 |
| 32 | Direct Compression | — | 13.8 | — |
| 33 | Direct Compression | — | 13.8 | — |
| 36 | Granulation | 14.4 | 6.25 | — |
| 37 | Granulation | 13.3 | 6.45 | — |
| 38 | Granulation | 20.0 | 18.0 | — |
| 39 | Granulation | 6.9 | 1.67 | — |
| 40 | Granulation | 17.1 | 14.3 | — |
| 41 | Granulation | 18.0 | 16.7 | — |
| 42 | Granulation | 8.2 | 6.7 | — |
| 43 | Granulation | 15.0 | 14.3 | — |
| 44 | Granulation | 18.0 | 16.2 | — |
| 45 | Granulation | 15.5 | 12.7 | — |
| 46 | Granulation | 15.0 | 14.3 | — |
| 47 | Granulation | 20.0 | 14.3 | — |
| 48 | Granulation | 18.0 | 13.8 | — |
| 49 | Granulation | 18.0 | 16.7 | — |
| 50 | Granulation | 16.7 | 14.9 | — |

TABLE 2-continued

Flow rates and angles of repose for several AP-720 formulations

| Formulation | Process | Unlubricated Gran. Flow Rate (g/sec) | Lubricated Gran. Flow Rate (g/sec) | Angle of Repose |
|---|---|---|---|---|
| 51 | Direct Compression | 10.5 | 10.8 | 32 |
| 52 | Direct Compression | 14.7 | 10.2 | 28 |
| 53 | Direct Compression | no flow | no flow | no flow |
| 54 | Direct Compression | 2.85 | 2.38 | 24.2 |
| 55 | Direct Compression | no flow | no flow | no flow |
| 56 | Direct Compression | — | — | — |

— = measurement was not taken,
no flow = formulation would not flow for measurement to be taken 2) Preparation and Testing of Tablets Compression of granules into tablets was performed on a Stokes model E single punch tablet press using a 5/16 inch concave punch and die set. Tablet hardness was initially tested with a Pfizer hardness tester and later confirmed with a Schleuniger 6D hardness tester in batches of 10 tablets and was reported as the average hardness for the 10 tablets.

Tablet friability was determined for batches of 10 tablets with a Vanderkamp friabilator operating at normal speed for 100 revolutions. Tablet friability was reported as an average of the weight loss for the 10 tablets.

Tablet weight variation was obtained with a Ultra Balance ® electronic checkweigher. Statistical analysis of the data was also performed by this instrument.

Content uniformity of the experimental formulation was performed by dissolving 10 individual tablets and subsequently determining the UV absorbance with a Hewlett-Packard 8451A diode array spectrophotometer. Concentration and the amount of drug per tablet were determined by comparing the above data with a standard. Physical properties of the resulting tablets is depicted in Table 3.

TABLE 3

Physical properties of AP-720 conventional release formulations and non-drug containing formulations

| Formulation | Bulk Density (g/cc) | Tap Density (g/cc) | Friability (%) | Hardness (lbs) | Weight (mg) (variance) | Loss on Drying | Process |
|---|---|---|---|---|---|---|---|
| 6 | 0.358 | 0.413 | varies | varies | 300 | — | dc |
| 7 | 0.406 | 0.433 | varies | varies | 300 | — | dc |
| 8 | 0.406 | 0.433 | varies | varies | 300 | — | dc |
| 9 | 0.587 | 0.643 | 0.13 | 13.8 | 100.3 (2.0) | 2% | g,c |
| 36 | 0.526 | 0.625 | varies | varies | 300 | — | g,c |
| 37 | 0.527 | 0.523 | varies | varies | 300 | — | g,c |
| 38 | 0.601 | 0.646 | varies | varies | 300 | — | g,c |
| 39 | 0.487 | 0.546 | varies | varies | 300 | — | g,c |
| 40 | 0.488 | 0.541 | varies | varies | 300 | — | g,c |
| 41 | 0.477 | 0.527 | varies | varies | 300 | — | g,c |
| 42 | 0.526 | 0.556 | varies | varies | 300 | — | g,c |
| 43 | 0.608 | 0.626 | varies | varies | 300 | — | g,c |
| 44 | 0.626 | 0.646 | varies | varies | 300 | — | g,c |
| 45 | 0.542 | 0.556 | varies | varies | 300 | — | g,c |
| 46 | 0.528 | 0.557 | varies | varies | 300 | — | g,c |
| 47 | 0.599 | 0.628 | varies | varies | 300 | — | g,c |
| 48 | 0.50 | 0.527 | varies | varies | 300 | — | g,c |
| 49 | 0.571 | 0.588 | varies | varies | 300 | — | g,c |
| 50 | 0.606 | 0.645 | varies | varies | 300 | — | g,c |
| 51 | 0.406 | 0.433 | varies | varies | 300 | — | dc |
| 52 | 0.666 | 0.698 | varies | varies | 300 | — | dc |
| 53 | 0.358 | 0.413 | varies | varies | 300 | — | dc |
| 54 | 0.355 | 0.406 | varies | varies | 300 | — | dc |
| 55 | 0.326 | 0.428 | varies | varies | 300 | — | dc |

— = measurement was not taken,
g = granulation,
c = compression,
dc = direct compression,
varies = value will vary depending upon the compression force applied Assay of both the experimental and commercial formulations was performed by triturating 20 tablets and weighing the equivalent of one tablet. The samples are analyzed on a UV spectrophotometer. Concentration and the amount of drug per tablet were determined by comparing the above data with a standard.

Disintegration of experimental and commercial chlorpheniramine maleate tablets (Geneva Generics) was performed with the disintegration apparatus (Erweka) in distilled water at 37° C. Disintegration time was recorded when the last particle passes through the #10 mesh screen in the basket of the apparatus.

The dissolution of drug from both the experimental and commercial tablets was determined using a Hanson Research model 72 dissolution apparatus by USP method 2. The dissolution media was distilled water at a volume of 500 ml. The paddle speed was 50 rpm with a temperature of 37° C. Samples were drawn and analyzed after 45 minutes with a Hewlett-Packard 8451A diode array spectrophotometer and were reported as an average of 3 doses. Concentration was determined by comparing the above data with a standard.

The data for the experimental tablets was compared to commercial chlorpheniramine maleate tablets as far as disintegration, dissolution and assay are concerned. The same procedures were utilized for each such tablet formulation. Direct compression methods are discussed below.

B) Sustained Action Tablets

A chosen approach to developing a sustained release dosage form started with the investigation of formulations that incorporate a water insoluble bulking agent. This type of system is considered a matrix release system in which insoluble ingredients remain intact and drug must diffuse through the dosage form to become available for dissolution. An insoluble filler (dicalcium phosphate) was selected for use in this type of dosage form. The effects of formulation and processing factors were tested on the dosage forms to establish which variables exist for this system.

Another approach to the development of a sustained release dosage form with AP-720 involved the use of this protein as a vehicle for direct compression. A problem that had to be solved before AP-720 could be used as a vehicle for sustained release tablets was enhancement of it's flow rate. AP-720 is manufactured in the form of a powder. The powder is resistant to flow and would not be a good candidate to use in a high-speed tablet press. Granulation of AP-720 allowed for the increase in particle size that is needed to enhance flow rates to an acceptable level. Compression properties of the granulated protein are also enhanced over that of the powder form as stronger tablets were produced when both are compressed at equal pressures. The effects of formulation and processing factors were tested on the dosage forms to establish which variables exist for this system.

1) AP-720/Dicalcium Phosphate Systems

Dicalcium phosphate and AP-720 based formulations required wet granulation to form suitable particles for high-speed compression, A suitable formulation was tested for granulation properties and in vitro release, For example, formulation 10 is discussed, Chlorpheniramine maleate was again used as model drug because of its high water solubility and low normal dose which should not affect the overall properties of the formulation, The components are shown below,

| Substance | Concentration | Use |
|---|---|---|
| Dicalcium phosphate | 244 mg | Bulking agent |
| Chlorpheniramine maleate | 8 mg/tablet | Active |
| AP-720 | 15% (w/w) | Binder |
| Magnesium stearate | 1% (w/w) | Lubricant/Glidant |
| Distilled water (55 ml) | | Wetting agent |

Tablet weight = 300 mg
Batch size = 300 grams
Theoretical Yield = 1000 tablets a) Preparation of Granules Granulation of the above formulation was performed by conventional massing and screening techniques, The active drug substance, dicalcium phosphate (Fisher Scientific) and AP-720 were initially mixed in a twin shell blender (Patterson-Kelly Co. Inc. model LB-1384) for 10 minutes and transferred to a planetary mixer (Hobart) and mixed for an additional 5 minutes. Water was slowly added to the powder mixture (over a period of 5 minutes) while mixing at low speed. The resultant mass was manually passed through #12 mesh screen and dried overnight at 40° C. in a Stokes vented tray drying oven. The granules formed were passed through #20 mesh screen with the aid of an Erweka oscillating granulator. The reduced granules were tested for flow rate, angle of repose, along with bulk and tap density and loss on drying. Magnesium stearate (Ruger) was then added and mixed in a twin shell blender for 10 minutes. The lubricated flow rate was then determined. Table 2 gives the flow rate information.

The pressure-hardness profile and the assessment of compaction behavior were determined by manual compaction of the formulations in a Carver laboratory press in which force application can be monitored. The granules were compressed at 4 different pressures (1,000, 2,000, 3,000, 4,000 psi) with a dwell time of 3 seconds. It is found that these pressures give realistic tablet hardness in granule pretests. Tablet hardness was determined using a Schleuniger tablet tester 6D in batches of 10 tablets and was reported as the average hardness for the 10 tablets.

Tablet friability was determined for batches of 10 tablets with a Vanderkamp friabilator operating at normal speed for 100 revolutions. Tablet friability loss was reported as an average of the weight loss for the 10 tablets.

The dissolution of chlorpheniramine maleate from the tablets was determined using USP method 2. The dissolution media was distilled water at a volume of 500 ml. The paddle speed was set at 50 rpm and run at a temperature of 37° C. Samples were analyzed at 262 nm and are reported as an average of 3 tablets. Assay of AP-720 tablets was performed by triturating 20 tablets and weighing back the equivalent of one dosage unit. This powder was dissolved in 100 ml of distilled water and passed through a 0.45 m millipore filter before sampling. Standards were prepared with pure drug and was used to interpret absorbance values. The percent released versus time was reported for each formulation.

TABLE 4

Physical properties of AP-720 sustained release formulations

| Formulation | Bulk Density (g/cc) | Tap Density (g/cc) | Friability (%) | Hardness (lbs) | Weight (mg) (variance) | Loss on Drying | Process |
|---|---|---|---|---|---|---|---|
| 1 | — | — | — | — | 314.2 | — | g,c |
| 2 | — | — | 0.47 | 15.78 | 300 | — | dc |
| 3 | — | — | — | — | 309 | — | g,c |
| 4 | 0.45 | 0.546 | 0.236 | 19.04 | 213 (1.92) | — | dc |
| 5 | — | — | — | — | 328 | — | g,c |
| 10 | 0.81 | 0.84 | varies | varies | 300 | 2% | g,c |
| 11 | 0.81 | 0.84 | 0.31 | 24.8 | 300 | — | g,c |
| 12 | 0.80 | 0.83 | 0.25 | 26.8 | 300 | — | g,c |
| 13 | 0.80 | 0.82 | 0.35 | 23.6 | 300 | — | g,c |
| 14 | 0.81 | 0.87 | 0.37 | 18.5 | 300 | — | g,c |
| 15 | — | — | 0.47 | 14.4 | 300 | — | dc |
| 16 | — | — | 0.30 | 21.1 | 273.8 | — | dc |
| 17 | — | — | 0.36 | 21.7 | 282.6 | — | dc |
| 18 | — | — | 0.45 | 18.3 | 300 | — | dc |
| 19 | — | — | 0.36 | 17.6 | 294.9 (3.0) | — | dc |
| 20 | — | — | 1.56 | 12.5 | 271.0 (3.7) | — | dc |
| 21 | — | — | 0.27 | 20.8 | 265.0 (4.4) | — | dc |
| 22 | — | — | 0.47 | 15.8 | 300 | — | dc |
| 23 | 0.45 | 0.54 | 0.24 | 19.0 | 213.0 (1.9) | 3% | dc |
| 24 | — | — | 0.15 | 24.7 | 223.4 (0.9) | — | dc |
| 25 | — | — | 0.14 | 25.9 | 222.8 (1.1) | — | dc |
| 26 | — | — | 0.17 | 25.8 | 223.4 (4.3) | — | dc |
| 27 | 0.45 | 0.546 | 0.24 | 19.0 | 213.0 (1.9) | 3% | dc |
| 28 | 0.45 | 0.546 | 0.24 | 19.0 | 213.0 (1.9) | 3% | dc |
| 29 | — | — | 0.14 | 25.9 | 222.8 (1.1) | — | dc |
| 30 | — | — | 0.14 | 25.9 | 222.8 (1.1) | — | dc |
| 31 | — | — | varies | varies | 200 | — | dc |
| a | — | — | varies | varies | 200 | — | dc |
| b | — | — | varies | varies | 200 | — | dc |
| c | — | — | varies | varies | 200 | — | dc |
| d | — | — | varies | varies | 200 | — | dc |
| e | — | — | varies | varies | 200 | — | dc |
| 32 | 0.454 | 0.546 | 0.23 | 19.0 | 213.0 (1.9) | 3% | dc |
| 33 | 0.454 | 0.546 | 0.23 | 16.2 | 200.8 (2.0) | 3% | dc |
| 56 | — | — | 0.14 | 25.6 | 197.7 | — | dc |

— = measurement was not taken,
g = granulation,
c = compression,
dc = direct compression,
varies = value will vary depending upon the compression force applied Table 4 describes the physical properties of the sustained release formulations. Formulations 1, 3, 5, and 10–14 represent granulation with dicalcium phosphate.

2) Direct Compression

Eight tablet formulations were prepared and tested for their physical characteristics and tablet properties in a sustained release direct compression system. Chlorpheniramine maleate, anhydrous theophylline, acetaminophen APAP (Ruger) and phenylpropanolamine HCL PPA (Sigma Chem. Co.) were model drug substances used in the formulations. These drug substances were chosen because of their aqueous solubility and compression characteristics.

a) Preparation of AP-720 Granules

Granular AP-720 was prepared by conventional massing and screening techniques. Granulating this substance was conducted by mixing 135 ml of distilled water with 300 grams of AP-720. The mass was tray dried at 40° C. for 4 hours and passed through an Erweka oscillating granulator with a #20 mesh screen. The fines were eliminated by sieving the granules through #80 mesh screen. The remaining granules were used for tablet compression. The compression versus tablet crushing force was performed to assess the compaction behavior of AP-720 granules. The granules were compressed in a Carver laboratory press at 3 different pressures (1,000, 2,000, 3,000 psi) with a dwell time of 3 seconds.

Tablets were prepared by simply mixing the AP-720 granules, drug and magnesium stearate, to lubricate the powder mixture, in a twin shell blender. Compression of the formulation into tablets was performed on a Stokes model E single punch tablet press using a 5.75 mm flat punch and die set. Tablet hardness was initially tested with a Pfizer hardness tester and later confirmed with a Schleuniger 6D tablet hardness tester in batches of 10 tablets and was reported as the average hardness for the 10 tablets.

Tablet friability is determined for batches of 10 tablets with a Vanderkamp friabilator operating at normal speed for 100 revolutions. Tablet friability loss is reported as an average of the weight loss for the 10 tablets. Referring back to Table 3, formulations 2, 4, and 15–56 represent direct compression systems, 15–22 were sustained release formulations.

EXAMPLE 1

MOISTURE UPTAKE OF PURIFIED ANIMAL PLASMA

A common procedure in the evaluation of an excipient for any dosage form is to obtain the moisture uptake of the substance. The amount of moisture a substance absorbs during storage can be of significance if the formulation is exposed to these conditions for extended time periods. Moisture level plays a part in overall stability of the formulation that contains the binder as moisture sites are thought to be the "seed" for drug degradation. This was performed by placing a known amount of a substance in a controlled humidity and temperature chamber for a specified period of time. A hot pack ™ Model 434304 Temperature-Humidity Chamber was used to expose the powders to the controlled environment. Moisture uptake was determined gravimetrically after adequate exposure time. AP-720 (purified spray dried pig plasma) was compared to several other traditional binders and AP-100 (plasma from another animal source). The other binders included Avicel PH102 (FMC Corp.), (microcrystalline cellulose) and PVP-40 (Sigma Chemical Co.). Formulations tested were formulas 1–8.

Each substance was dried to a constant weight by drying at 35° C. for five days before exposure in the humidity chamber. Samples were weighed and placed in the humidity chamber set at 25° C. and withdrawn and weighed after 48 hours exposure. Relative humidity used for this study was 30, 40, 53, 60, 70 and 80%.

Figure 1:
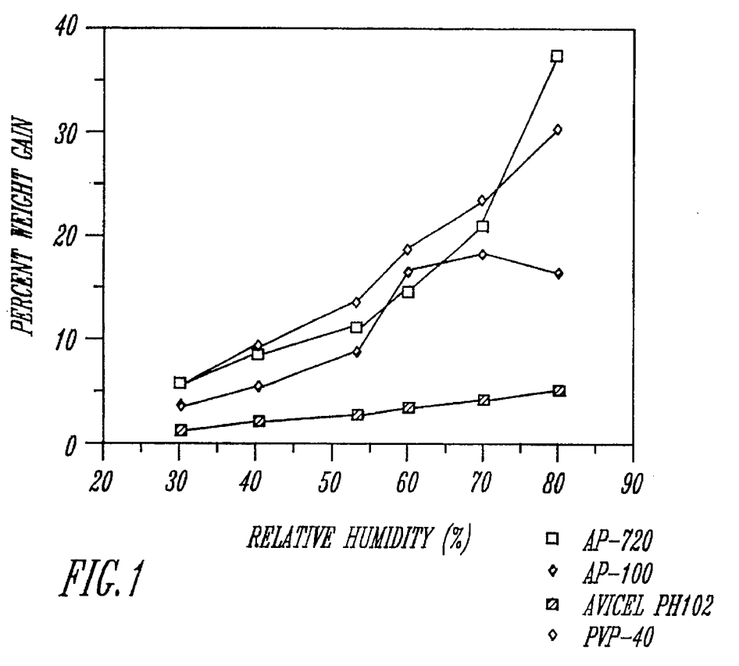
FIG. 1 is a graph of moisture sorption for experimental tablet binders.

Results of this procedure are represented graphically in FIG. 1. It can be seen that Avicel PH102 absorbs very little moisture when compared to the other binders. AP-720 is comparable to PVP-40 for moisture uptake. As can be seen, AP720 presents acceptable moisture absorption ranges, for use in pharmaceutical compositions.

EXAMPLE 2

FLOW CHARACTERISTICS

Testing of a tablet formulation requires evaluation of several parameters. The granulation must be tested before compression to assess possible problems that could occur during tableting.

One important granulation parameter that must be considered in tablet formulation is the flow rate of the formulation. This can affect several parameters of the final tablet formulation. Poor formulation flow rates may facilitate an uneven fill in the die cavity causing tablet weight variation, drug content variability as well as hardness and friability differences. Flow rates of AP-720 formulations were determined by passing a 100 gram sample through a standard glass funnel and timing the rate of passing. Further, a lubricating agent which is often added in tablet formulation to aid in processing by keeping the compacted material from sticking to the punches and die post compression was added. A common lubricant, magnesium stearate is normally used. The unlubricated and lubricated flow rates were examined for several formulations.

Yet another granulation parameter, the angle of repose gives an indication of how particles pass across each other during processing. The angle of repose is measured by aligning 100 grams of unlubricated granules to form a heap on the flat surface. Height and radius of the heap is measured and the angle of repose is calculated by equations known to those of skill in the art. An angle of repose less than 30° is thought to be adequate for proper flow properties in which granules will freely flow across one another. Flow rates and angles of repose for several formulations were evaluated. Table 2 represents the flow rates and angle of repose for several of these formulations. As can be seen the granulation process seems to enhance the flow of the formulations considerably. Granular AP-720 as a direct compression vehicle does enhance the flow characteristics of many non-flowing substances. The "no flow" formulations incorporate a non-flowing drug substance in such high concentration that the flow rate is considerably slowed. These formulations may require a force feed hopper for consistent die fill.

The flow rates of the lubricated granulation were usually slower than those for the unlubricated. This is expected as the lubricant magnesium stearate is a substance that is resistant to flow and may decrease the flow rates of formulations that contain it. Even with the decrease in the flow rate post lubrication the flow rates of greater than 5 grams per second have shown to be adequate for use in the Stokes Model E single punch tablet press (output=approximately 40 tablets/minute) or Colten model 204 four station rotary tablet press (output=approximately 160 tablets/minute). Granular AP-720 does enhance the flow rates of poor flowing substances for direct compression usage.

The angles of repose for most of the above formulations fall within the less than or equal to 30 degrees range indicating good flow characteristics. Even a formulation that has a greater than 30 degree angle of repose may still be used with some cautions. Thus it can be seen that AP-720 (spray dried animal plasma) exhibits significant beneficial flow characteristics for use as a tablet binder. Further it was shown that AP-720 also may be used as a direct compression vehicle in that it enhances the flow characteristics of many non-flowing substances.

EXAMPLE 3

COMPRESSION PROPERTIES

A) Solution Binding

Various tablets were tested for their compression properties and compared to other formulations. This example did a side by side comparison of AP-720 and other common binders. Table 5 depicts the formulations using other direct compression and solution binders.

TABLE 5

| | | | | | | | | | | | | |
|---|---|---|---|---|---|---|---|---|---|---|---|---|
| | | | | | direct compression and solution binders | | | | | | | |
| No | AP-720 | Avicel® PH101 | Acacia | Gelatin | HPMC | PVP-40 | CPM | Lactose NF | THEO | Mag. Stearate | AcDiSol® | Process |
| 6 | — | 300 mg | — | — | — | — | — | — | — | — | — | dc |
| 7 | 300 mg††† | — | — | — | — | — | — | — | — | — | — | dc |
| 8 | 300 mg††† | — | — | — | — | — | — | — | — | — | — | dc |
| 36 | 6 mg | — | — | — | — | — | 8 mg | 280 mg | — | 3 mg | 3 mg | g,c |
| 37 | 15 mg | — | — | — | — | — | 8 mg | 271 mg | — | 3 mg | 3 mg | g,c |
| 38 | 21 mg | — | — | — | — | — | 8 mg | 265 mg | — | 3 mg | 3 mg | g,c |
| 39 | — | 6 mg | — | — | — | — | 8 mg | 280 mg | — | 3 mg | 3 mg | g,c |
| 40 | — | 15 mg | — | — | — | — | 8 mg | 271 mg | — | 3 mg | 3 mg | g,c |
| 41 | — | 21 mg | — | — | — | — | 8 mg | 265 mg | — | 3 mg | 3 mg | g,c |
| 42 | — | — | — | — | — | 6 mg | 8 mg | 280 mg | — | 3 mg | 3 mg | g,c |
| 43 | — | — | — | — | — | 15 mg | 8 mg | 271 mg | — | 3 mg | 3 mg | g,c |
| 44 | — | — | — | — | — | 21 mg | 8 mg | 265 mg | — | 3 mg | 3 mg | g,c |
| 45 | — | — | — | 6 mg | — | — | 8 mg | 280 mg | — | 3 mg | 3 mg | g,c |
| 46 | — | — | — | 15 mg | — | — | 8 mg | 271 mg | — | 3 mg | 3 mg | g,c |
| 47 | — | — | — | 21 mg | — | — | 8 mg | 265 mg | — | 3 mg | 3 mg | g,c |
| 48 | — | — | 6 mg | — | — | — | 8 mg | 280 mg | — | 3 mg | 3 mg | g,c |
| 49 | — | — | 15 mg | — | — | — | 8 mg | 271 mg | — | 3 mg | 3 mg | g,c |
| 50 | — | — | 21 mg | — | — | — | 8 mg | 265 mg | — | 3 mg | 3 mg | g,c |
| 51 | 198 mg | — | — | — | — | — | — | — | — | 2 mg | — | g,c |
| 52 | — | — | — | 198 mg | — | — | — | — | — | 2 mg | — | dc |
| 53 | — | 198 mg | — | — | — | — | — | — | — | 2 mg | — | dc |
| 54 | — | — | — | — | — | 198 mg | — | — | — | 2 mg | — | dc |
| 55 | — | — | — | — | 198 mg | — | — | — | — | 2 mg | — | dc |
| 56 | — | — | — | — | 99.8 mg | — | — | — | 100 mg | 2 mg | — | dc | g = granulation,
c = compression,
dc = direct compression,
† = distribution,
††† = 60/80 mesh fractions Four commonly used binders along with experimental binder were investigated. Binders tested included AP-720, Gelatin USP (Fisher Scientific), acacia gum powder (Ruger), Polyvinyl pyrrolidone PVP-40 and microcrystalline cellulose (Avicel® PH 101). All binders were placed in solution with distilled water at a volume of 50 ml. Lactose NF was used as a bulking agent and chlorpheniramine maleate was the active drug in formulations studied. (Formulations used were formulations 36–50).

Figure 2:
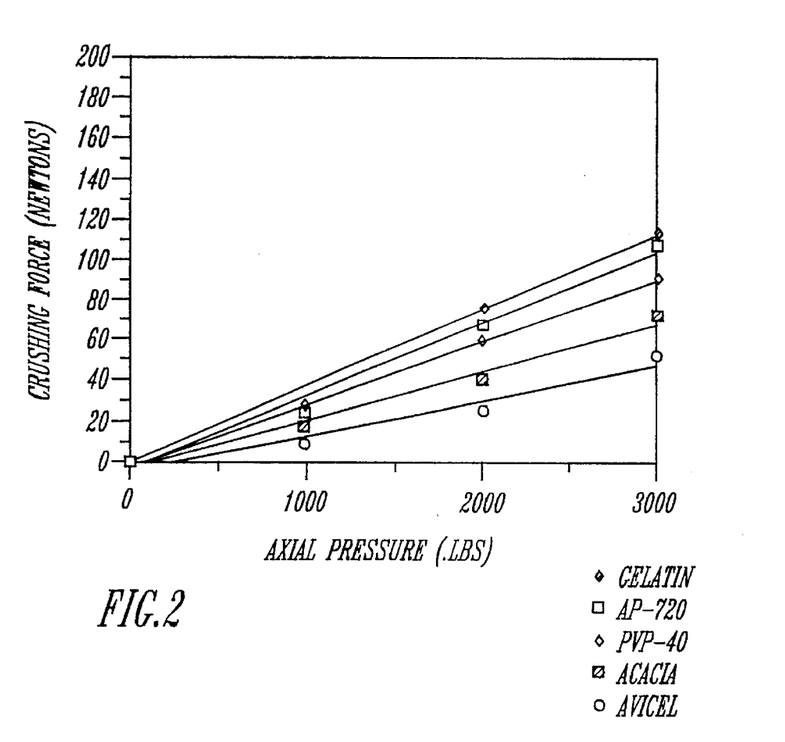
FIG. 2 is a graph of crushing force versus applied pressure for various solution binders.

Granulation of the described tablets was conducted by massing and screening techniques. The lactose, drug and 0.5% AcDiSol® (FMC Corp.) were initially mixed in a twin shell blender for 10 minutes and transferred to a planetary mixer (Hobart) and mixed for an additional 5 minutes. The solution was prepared with each binder by increment stirring and heating at 40° C. Binder solutions were slowly incorporated into the powder mixture over a period of five minutes while mixing at low speed. Resultant mass was manually passed through a no. 12 mesh screen and subsequently dried overnight at 40° C. in a Stokes vented tray drying oven. The granules formed were passed through a no. 20 mesh screen with the aid of an Erweka oscillation granulator. The reduced granules were tested for flow properties, along with bulk and tap density. See Table 3. Magnesium stearate and the remaining AcDiSol® were added and mixed in a twin shell blender for ten minutes. The lubricated flow rate was then determined. See Table 2. The pressure hardness profile in the assessment of compaction behavior were determined by manual compaction in a Carver Laboratory press in which force application was monitored. Tablet hardness, friability and dissolution experiments were performed as well. Table 3. FIG. 2 represents tablet crushing force versus applied pressure for the 5 percent w/w solution binders, formulations 37, 40, 43, 46, and 49. This profile is also representative of the 2 and 7 percent w/w solutions. (FIG. 2). As can be seen from FIG. 2, AP-720 also exhibits excellent binding capacity and tablet strength when compared to other solution binders tested.

B. Direct Compression Binder Testing

Five tablet binders including AP-720, (formulation 51), granulated gelatin USP (formulation 52) Avicel® pH 101 (formulation 53), polyvinylpyrrolidone PVP-40 (formulation 54) and hydroypropylmethyl cellulose HPMC K15M (Dow Chemical Co.) (formulation 55) were tested as direct compression vehicles (Table 5). All binders were equally mixed with one percent w/w magnesium stearate to lubricate the formulation. Pressure hardness profile and assessment of compaction behavior were determined by manual compaction with a Carver Lab Press, in which force application could be monitored. The formulations which force application could be monitored. The formulations were compressed at two different pressures, 1000 and 2000 PSI, with the dwell time of 3 seconds. Tablet hardness and friability were determined by standard methods. Table 3.

Figure 3:
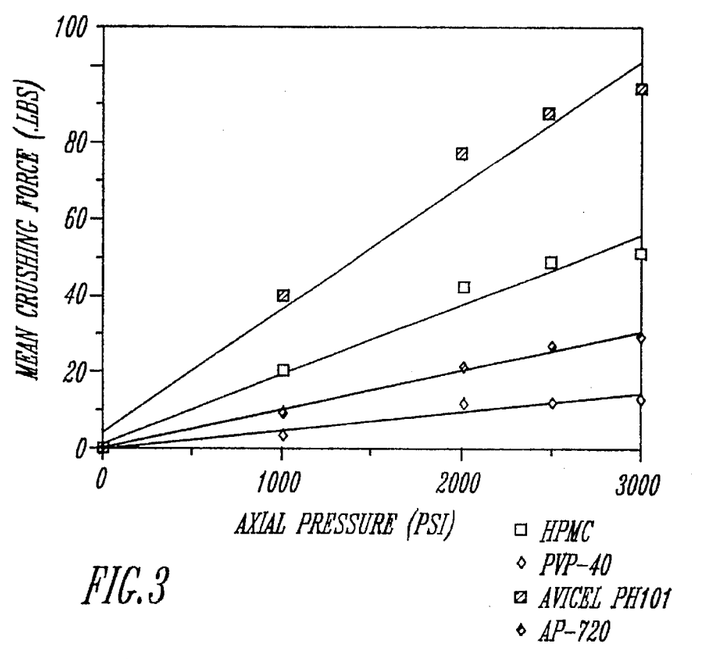
FIG. 3 is a graph of crushing force versus applied pressure for various direct compression binders.

FIG. 3 represents the crushing force versus applied pressure for each of these formulations. Granular gelatin USP was not tested as it does not form strong compacts when compressed in a Carver Lab press at the above pressures. As the graph depicts, Granular AP-720 was comparable to known direct compression vehicles Avicel pH 101®, PVP 40, and HPMC demonstrating its utility as a direct compression vehicle.

These properties were obtained by earlier described methods. The parameters outlined in Table 3 demonstrate that the experimental system release AP-720 formulations exhibit excellent formulation properties and act properly in processing and compression. The tablets formed have low friability and excellent hardness, which is important parameter. Further, the tablets have low loss on drying demonstrating that drying of the granules is complete before further processing. Table 3.

EXAMPLE 4

RELEASE MODEL TESTING & DRUG LOAD EFFECTS

The primary method of in vitro testing involves utilization of dissolution for drug release profiles. specified media using an approved apparatus for specific periods of time. Conventional release AP-720 tablets are expected to conform with respect to dosage form monograms when tested under the same conditions. Sustained released AP-720 tablets are expected to release drug over a period of at least eight hours. Effect of drug load must be considered in dosage form design, it is possible that an increase in drug load will increase the rate of drug release from a tablet dosage form. Tablets should deliver the drug steadily for a designed period of time with sustained release tablets expected to release over a period of at least 8 hours. Control of drug release may be manipulated by the concentration of AP-720 to drug in ratio which are greater than or equal to 1:1 protein to drug, are thought to be needed for controlled release.

Release testing of tablets granulated with water soluble filler (lactose) showed an immediate release of the active drug substance. When dicalcium phosphate was combined with AP-720 a complex, insoluble matrix was formed. This matrix allows for slow release of the drug into the dissolution media. AP-720 forms a hydrogel which physically entraps the drug molecules. In order for the drug to be available in solution, the drug must have diffused through the gel layer or pass freely by erosion or relaxation of the gel barrier. This is known as a hydrogel system and it is proposed mechanism of drug release.

The dissolution of drug from the tablets was determined using a Hanson Research model 72 dissolution apparatus by USP method 2. The dissolution media was distilled water (500 ml) for formulations 11–13. Potassium chloride solutions of 0.05 M, 0.1 M and 0.5 M were utilized to determine the release of chlorpheniramine maleate from the formulation at different ionic strengths. The paddle speed was 50 rpm and the temperature was 37° C. for all formulations. Assay of AP-720 tablets was performed by triturating 20 tablets and weighing back the equivalent of one dosage unit. This powder was dissolved in 100 ml of distilled water and passed through a 0.45 filter before sampling. Standards were prepared with pure drug and were used to interpret absorbance values. The percent released versus time was reported for each formulation.

Figure 4:
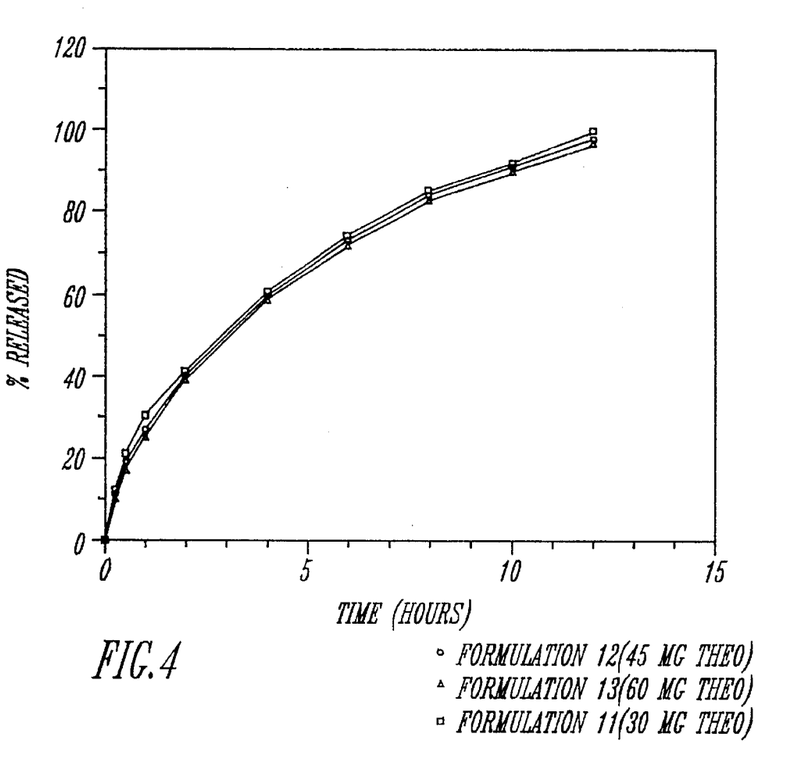
FIG. 4 is a graph depicting the release profiles for various drug loads for granulated sustained release tablets.

FIG. 4 represents the release profiles for formulations 11–13 sustained release with dicalcium phosphate by conventional dissolution methods. It can be seen that dissolution profiles are very similar at all concentrations and shows sustained release, even at drug and binder ratios of 1:1 (formulation 12) and 1.3:1 (formulation 13). It appears that drug load can exceed binder concentration and maintain sustained release for the respective systems.

The effective drug load versus binder concentration seems to have little effect on dissolution profiles for the above tested formulations, indicating the excellent ability of AP-720 to act as a sustain release binder.

For direct compression sustain release systems, the direct compression vehicle was enlarged in excess of the drug substance for low to moderate dose tablet dosage forms. Water insoluble filler was eliminated from the dosage form to test AP-720 release kinetics. Release profiles obtained for chlorpheniramine maleate tablets (formulations 15–17) and acetaminophen tablets (formulations 18–20) were tested for in vitro release by standard methods. Once again all release profiles were very similar, indicating that drug load at this range had little effect on percent of medicament released over time from AP-720 direct compression sustained release tablets. Within the concentration range tested, drug load and binder concentration has little effect on dissolution profiles.

Finally, another example was run using anhydrous theopylline drug load on release form of AP-720 direct compression matrix release systems. (formulations 24–26). Drug release, again, was not significantly affected by drug load in this range. Even at 50% drug load (formulations 26) there was still sustained release over a 12 hour testing period.

Figure 5:
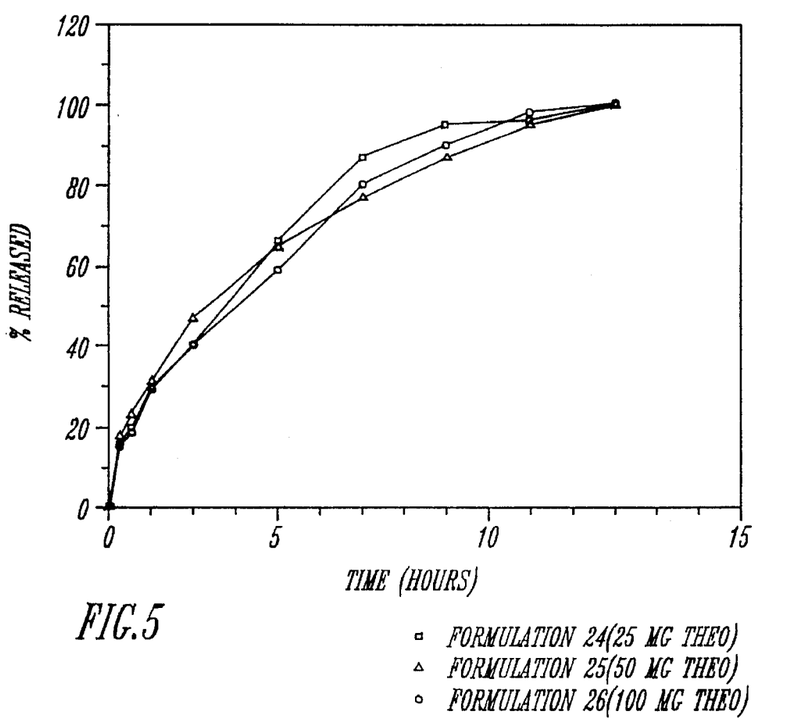
FIG. 5 is a graph depicting release profiles for various drug loads for direct compression sustained release tablets.

FIG. 5 demonstrates the effect of anhydrous theopylline drug load on release form. From the above examples it can be seen that the varying drug load of several different substances, of different solubility, does not significantly affect the percent released versus time profiles. Drug release is dependent upon the tablet remaining as a single unit and not disintegrating.

EXAMPLE 5

RELEASE MODEL TESTING - DISSOLUTION MEDIA

The human GI system is an environment dependent upon many variables. Fluctuations of pH and ionic strength, which naturally occur, could cause major changes in dosage forms release patterns. The same release formulations should be designed to release drug substances independently of the media they are exposed to. These experiments address the release profiles of AP-720 matrix release systems in different dissolution media. Dissolution media was changed and the release of the drug was studied over time.

The dissolution of chlorpheniramine maleate and anhydrous theophylline from the tablets was determined using a Hanson Research model 72 dissolution apparatus by USP method 2. The dissolution media included distilled water, 0.1N HCL solution, KCl solutions and simulated GI environment at a volume of 500 ml. The paddle speed was set at 50 rpm and run at a temperature of 37° C. The KCl solutions were composed of 0.01 M, 0.1 M and 0.5 M concentrations for different ionic strengths. The simulated GI environment involved 2 hours exposure to an acid media (0.1N HCL) and then buffering this solution to pH 6.8 with a 0.2 M tribasic sodium phosphate solution. Samples were analyzed with a Hewlett-Packard 8451A diode array spectrophotometer and were reported as an average of 3 tablets. The absorbance values were entered into a customized spreadsheet for computer assisted data analysis. Assay of AP-720 tablets was performed by triturating 20 tablets and weighing back the equivalent of one dosage unit. This powder was dissolved in 100 ml of distilled water and passed through a 0.45 m filter before sampling. Standards were prepared with pure drug and were used to interpret absorbance values. The percent released versus time was reported for each formulation.

Figure 6A:
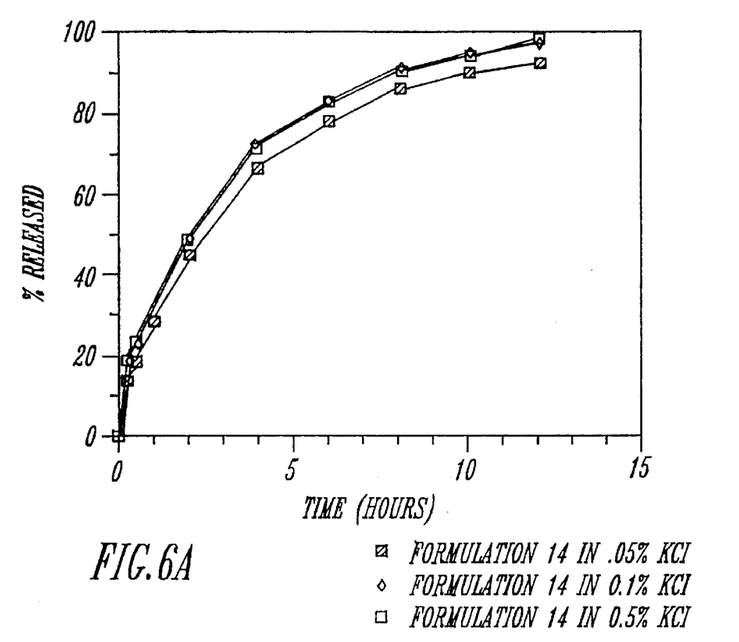
FIG. 6A is a graph depicting the release profiles for AP-720/dicalcium phosphate matrix system in different ionic strength media.

Two types of sustained release AP-720 formulations were tested for their release profiles in different dissolution media. These systems were the AP-720 - dicalcium phosphate granulation compression system (formulation 17) and AP-720—direct compression systems. (formulations 25 and 32). Changes in pH and ionic strength as well as the apparent pKa can change molecular conformation and solubility of proteins and could thus affect release profiles. Tested release profiles for formulation 14, a single chlorpheniramine maleate tablet formulation and dissolution media of potassium chloride at 0.05%, 0.1% and 0.5% demonstrated no significant change in release patterns. See FIG. 6A. Simulated gastric and intestinal fluid have an ionic strength of at least 0.1. Thus, it can be seen that ionic strength has no significant effect on the release profile for chlorpheniramine maleate tablets and AP-720 dicalcium phosphate systems.

Effect of drug release of the AP-720 dicalcium phosphate system in 0.1N HCL solutions showed the same result as above with sustained release over a twelve hour testing period. This relationship should be similar for other formulations of similar excipient content.

Figure 6B:
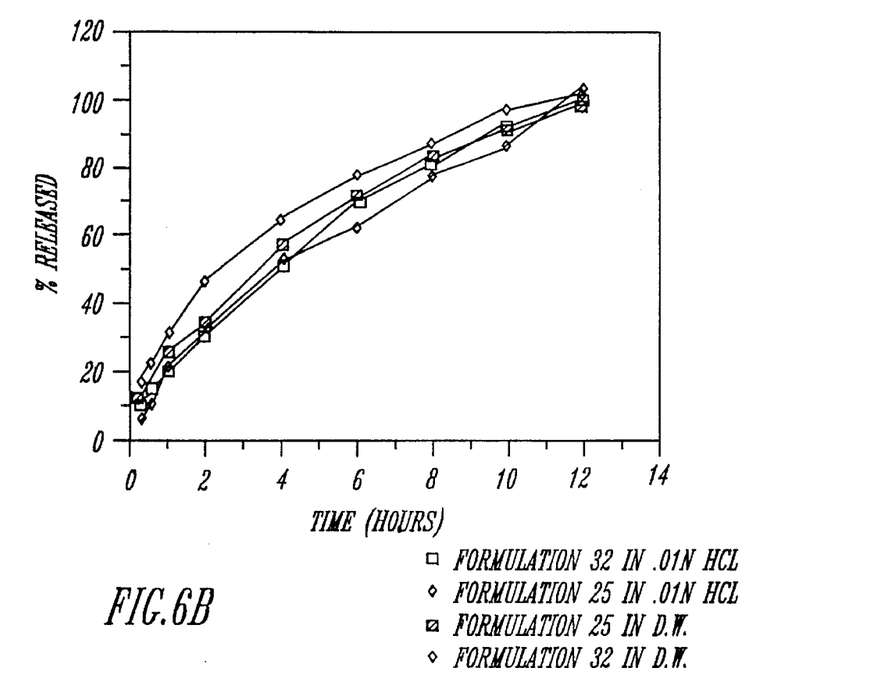
FIG. 6B is a graph depicting release profiles for direct compression AP-720 formulations in different media.

Release profiles for different dissolution media were also tested for the direct compression system. FIG. 6B represents release profiles for formulations 25 and 32 in distilled water and 0.1N in HCL solution. It can be seen that the release of the drug from the matrix is not significantly affected by the two different media. Acidic solutions can increase the release rate of certain matrix systems by disrupting the diffusion barriers and causing premature drug release. This phenomenon does not seem to be the case for this system. Its release profiles are similar for both 0.1N HCL solution and distilled water.

Dependence of drug release upon the ionic strength of dissolution media was tested using formulation 32 in distilled water and in 0.05, 0.1 and 0.5 molar potassium chloride. Once again there appeared to be no correlation between the ionic strength of the dissolution media and drug release.

Figure 7:
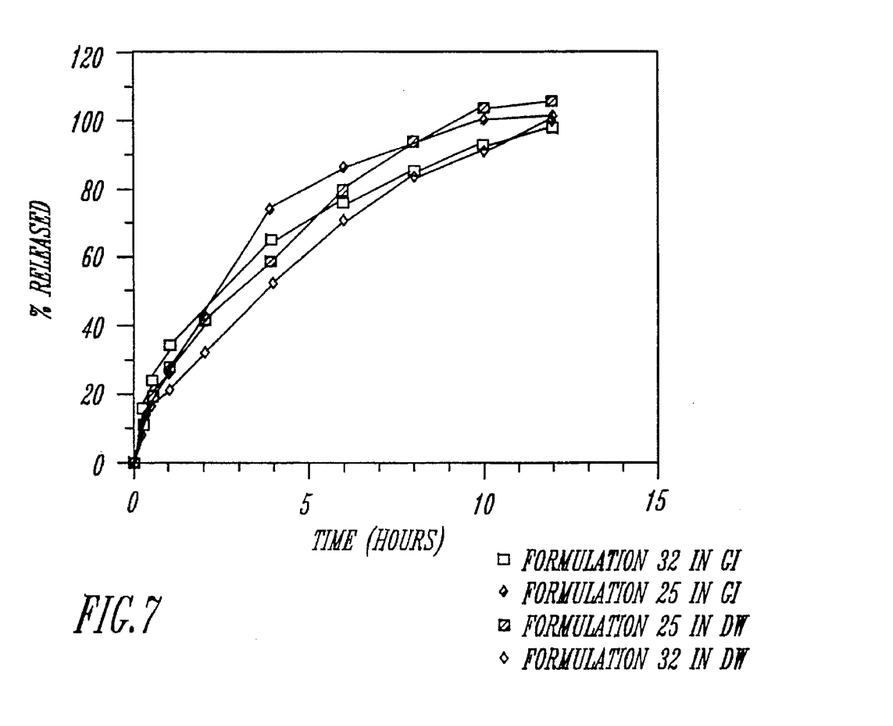
FIG. 7 depicts release profiles in simulated GI fluids.

FIG. 7 represents release of formulations 32 and 25 in a simulated GI environment. The tablets were exposed to two hours of acid media (0.1N HCL) and then buffered to a nearly neutral media (pH 6.8) with a 0.2 N tribasic sodium phosphate.

This procedure allows for a good look at how the release rates may be affected by the changes in pH in the intestine in vivo. It can be seen from FIG. 7 that the release of drug from the simulated GI environment, is not significantly different than that in distilled water. The dissolution media did not alter the release of these drug substances from the AP-720 matrix. This finding is predictable as it had already been seen that release was independent of pH and ionic strength.

EXAMPLE 6

RELEASE MODEL TESTING - COMPARISON

TO OTHER SUSTAINED RELEASE TABLETS

Formulations and compression of AP-720 and hydroxypropylmethylcellulose (HMPC matrix) release tablets, the current binder used in direct compression sustained release formulas, was compared. Both substances were used in direct compression systems. HPMC has been thought to be a promising hydrophillic polymer because it is directly compressible and hydrates rapidly at body temperature as well as acts independently of processing variables.

Two soluble matrixes were tested for active drug release by an in vitro dissolution test. Binder materials were tested for bulk density. AP-720 (formulation 26) and HPMC (formulation 56) were each mixed with 50% (w/w) anhydrous theopylline and 1% (w/w) magnesium sterate in a beaker to make two separate formulations. The batch formula for both formulations was 20 grams. Two formulations were compressed at 2,500 PSI in a Carver Laboratory Press, using a 5.75 mm flat punch and dye set. The tablet weight was 200 mg. A dwell time of 3 seconds was set for each tablet compression. Tablet hardness, friability and dissolution were determined once again.

Figure 8:
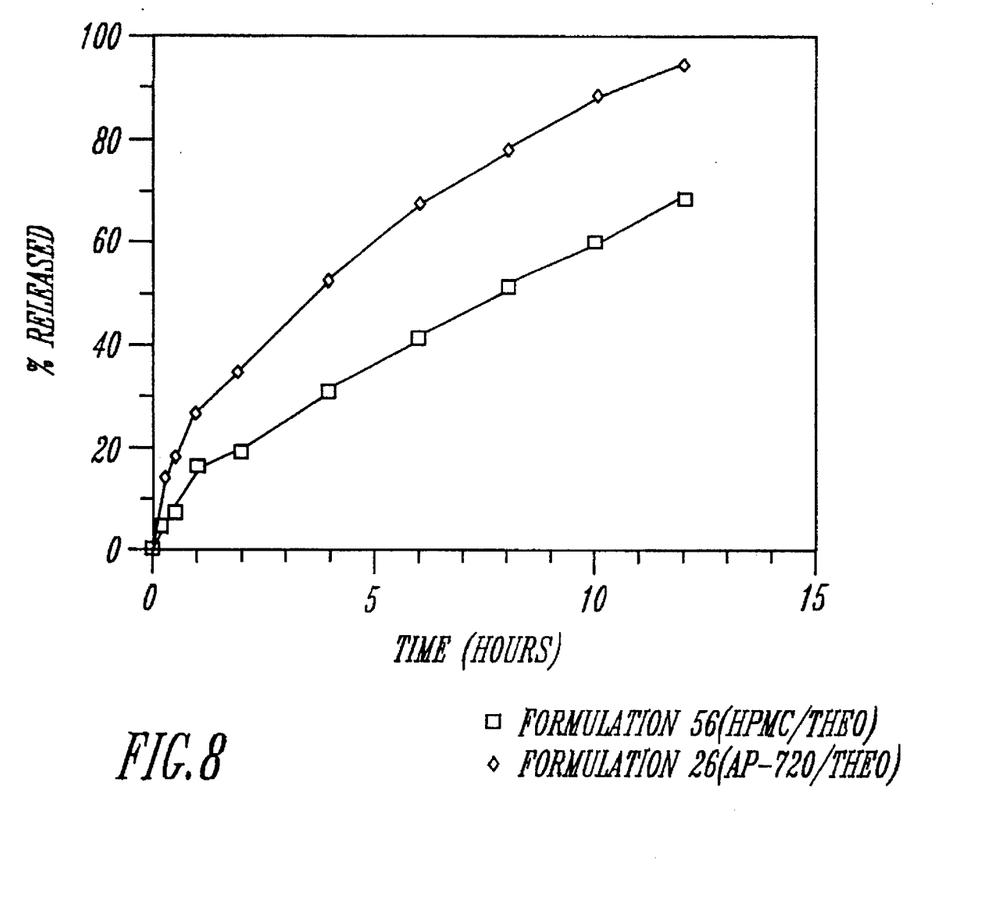
FIG. 8 depicts release profiles for direct compression AP-720 and hydroxypropylmethylcellulose formulations mixed with anhydrous theopylline and magnesium stearate.

Both formulations were tested in vitro release under the same conditions as earlier identified for release measurements. The results are shown in FIG. 8, which demonstrates significantly higher percent of medicament released over a twelve hour period for the AP-720 formula. Plots of percent versus time displayed in FIG. 8 were both HPMC formulation 56 and AP-720 formulation 26 systems. AP-720 matrix systems seem to release the active drug substance at a faster rate than HPMC matrix systems with 94% released after twelve hours of dissolution testing.

The HMPC matrix system allowed very slow drug release rates over the same twelve hour period. It was observed that both systems swelled to some extent and a gel barrier formed on the surface of the tablets after a short time in aqueous media.

After dissolution testing, the HMPC tablets still had a solid core containing drug binder and lubricant. It is postulated that the gel barrier formed around the HPMC tablets allowed only minor amounts of the dissolution media to penetrate and dissolve the active drug for diffusion controlled release. The AP-720 tablets, which may have higher amounts of pores due to larger particle size, allowed for efficient penetration of the dissolution media. With an increase in liquid penetration faster dissolution rates were seen.

From the above release profiles, it can be seen that the release of anhydrous theopylline is sustained for both AP-720 and HPMC matrix systems. Both binders displayed acceptable tablet properties when subjected to common tablet tests and sustained their release of anhydrous theopylline over an extended period of time. This comparison shows a more acceptable profile for AP-720 systems as unreleased drug after twelve hours in vivo may not be absorbed while passing through the human GI tract.

As the foregoing examples demonstrate, AP-720 (purified, spray dried animal plasma) exhibits excellent properties as a tablet binder. The examples demonstrate that the moisture uptake level is acceptable, compression force ranges are acceptable, as well as solution binder and direct compression binder testings. Further AP-720 shows exceptional promise as a sustained release system even better than the hydroxypropylmethylcellulose system currently used. The release of AP-720 has been shown to be independent of drug load and pH as well, indicating its likely utility for in vivo systems. As a tablet binding agent, AP-720 was shown to be comparable or better than many commonly used binders. Incorporation of AP-720 with the water insoluble filler, such as dicalcium phosphate, produced tablets that sustain drug release over a twelve hour period. This system was shown to release drug independently of the dissolution environment. It was further found that AP-720 could be granulated to enhance its full characteristics and compression properties. Use of the granulated form of AP-720 as a direct compression vehicle, revealed that the substance had definite potential to sustain drug release. Further investigation showed that the release of the drug from this system was independent of the pH of the dissolution media.

Further, the mechanism of drug release was investigated with AP-720 sustain release tablets. It was found that release of several types of drug substances was independent of pH and the system was independent of pH, and was able to sustain higher drug release percentages and thus more efficient usability than the HPMC binder.

Thus, it can be seen that the invention accomplishes at least all of its objectives.

What is claimed is:

1. A method of forming compressed tablet pharmaceutical compositions comprising: combining a medicament with an excipient, said excipient being purified, dried animal plasma 1a and compressing said combination to form a tablet wherein the medicament and the dried animal plasma are provided in an amount sufficient to maintain the tablet's shape and prevent crumbling.

2. The method of claim 1 wherein said animal is selected from the group consisting of a pig or a cow.

3. The method of claim 1 wherein said plasma is spray dried.

4. The method of claim 1 where said tablet is a sustained release tablet.

5. The method of claim 4 wherein said dried plasma is a direct compression vehicle.

6. The method of claim 4 wherein said composition contains a water insoluble filler.

7. The method of claim 1 wherein said excipient is used as a solution binder.

8. The method of claim 1 wherein said excipient is granulated.

9. The method of claim 8 wherein granulation of non-flowing substances with said plasma increases flow characteristics of said non-flowing substance, 10. The method of claim 1 wherein said excipient is used as a direct compression vehicle.

11. The method of claim 4 wherein said sustained release tablet has a release profile independent of drug load.

12. The method of claim 10 wherein said profile is independent of drug/excipient ratios of 1.3:1.

13. The method of claim 4 wherein said tablet release profile is independent of ionic strength of dissolution media.

14. The method of claim 4 wherein said tablet release profile is unaffected by the gastrointestinal environment.

15. The method of claim 5 wherein said sustained release tablet releases 94% of the pharmaceutical after 12 hours.

16. The method of claim 1 wherein said excipient is used as a binder.

17. A compressed tablet pharmaceutical composition comprising:

an active medicament and purified dried animal plasma in "a weight ratio sufficient to maintain the tablets shape and prevent crumbling".

18. The tablet of claim 17 wherein said plasma is spray dried.

19. The composition of claim 17 further comprising a solvent.

20. The composition of claim 17 further comprising a water insoluble filler.

21. The composition of claim 17 wherein said animal plasma is from a pig or cow.

22. The composition of claim 17 wherein said plasma is collected, purified and spray dried to form a powder.

23. A method of preparing a pharmaceutical tablet, said method comprising: drying purified animal plasma to form a powder; combining said plasma with an active medicament; and compressing said combination into a tablet for oral dosage wherein the medicament and the dried animal plasma are provided in an amount sufficient to maintain the tablet's shape and prevent crumbling.

24. The method of claim 23 wherein said drying is by spraydrying, drying.

25. The method of claim 23 further comprising granulating said powder before compression.

26. The method of claim 23 wherein said plasma is granulated with a non-flowing medicament.

27. The method of claim 23 wherein said combining is in solution.

28. The method of claim 23 wherein said tablet is a sustained release tablet.

29. The method of claim 28 further comprising combining a water insoluble filler with the plasma and medicament.

30. The method of claim 28 wherein said composition is a direct compression formulation.

31. The method of claim 28 wherein said tablet release profile is independent of ionic strength, acidity of dissolution media.

32. A method of forming compressed tablet pharmaceutical compositions comprising:

combining a medicament with an excipient, said excipient being purified, dried animal plasma, wherein the animal is selected from the group consisting of a pig or a cow, and;

compressing said combination to form a tablet.

33. A compressed tablet pharmaceutical composition comprising an active medicament and purified dried animal plasma, wherein the animal is selected from the group consisting of a pig or a cow, in an acceptable weight ratio so that the tablet maintains its shape and does not crumble.

* * * * *